United States Patent [19]

Ahrens et al.

[11] 4,031,236
[45] June 21, 1977

[54] NOVEL THIOPHENE DERIVATIVES AND THEIR PREPARATION

[75] Inventors: Hanns Ahrens; Helmut Biere; Clemens Rufer; Ralph Schmiechen; Eberhard Schroeder; Olaf Loge; Wolfgang Losert; Ekkehard Schillinger, all of Berlin, Germany

[73] Assignee: Schering Aktiengesellschaft, Berlin & Bergkamen, Germany

[22] Filed: May 20, 1975

[21] Appl. No.: 579,258

[30] Foreign Application Priority Data

May 21, 1974 Germany .......................... 2424742

[52] U.S. Cl. ........................... 424/275; 260/308 D; 260/332.2 A; 424/269
[51] Int. Cl.² ................. A61K 31/41; A61K 31/38; C07D 257/04; C07D 333/24
[58] Field of Search ............. 424/275; 260/332.2 A

[56] References Cited

UNITED STATES PATENTS

| | | | |
|---|---|---|---|
| 2,581,626 | 1/1952 | Brooks | 260/332.2 A |
| 3,560,525 | 2/1971 | Kaltenbronn | 260/332.2 A |

Primary Examiner—Frederick E. Waddell
Attorney, Agent, or Firm—Millen & White

[57] ABSTRACT

Thiophene derivatives of the formula

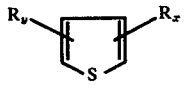

in which $R_x$ is —S—$CHR_5$—CONHOH or —S—$CHR_5$-5-tetrazolyl in which $R_5$ is H or alkyl of 1–6 carbon atoms and $R_y$ is 0–2 of alkyl or alkoxy of 1–6 carbon atoms or halogen, and their pharmacologically acceptable salts with bases, possess antilipolytic activity.

18 Claims, No Drawings

NOVEL THIOPHENE DERIVATIVES AND THEIR PREPARATION

BACKGROUND OF THE INVENTION

This invention relates to novel, antilipolytically active thiophene derivatives and to processes for the preparation and use thereof.

Pathologically high blood serum concentrations of triglycerides are held responsible, inter alia, for the origination and progression of arteriosclerotic changes of the blood vessel wall. The triglycerides in the serum originate not only from food intake but also from the liver, where they are synthesized from the blood, in part with the use of free fatty acids (FFA). A lowering of the FFA content in the serum results in a lowering of the triglyceride condentration in the liver and in the blood. BIZZI, VENERONI, and GARATTINI, J. Pharm. Pharmac. 18, 611, 1966; PAOLETTI and PUGLISI, Naunyn-Schmeidebergs Arch. Pharmak., 269, 317, 1971.

Since the FFA concentration in the serum depends primarily on the extent to which the triglyceride is split in the fatty tissue (lipolysis), a pharmacological inhibition of this process represents an effective measure for lowering the triglyceride level in the serum and to prevent arteriosclerotic changes of blood vessels. This was proven by animal experiments. BIZZI, VENERONI, and GARATTINI, J. Pharm. Pharmac. 18, 611, 1966; BIZZI, GARATTINI, VENERONI, HOWARD, GRESHAM, and JENNINGS, Atherosclerosis, in print, 1974. Also in humans, a reduction of the triglyceride concentration in the serum was measured after treatment with agents which inhibit lipolysis. BERINGER, BAENDER, GLANINGER, MAYRHOFER, and SCHNAK, Horm. Metab. Res. 2, 81, 1970.

Moreover, a reduction in the FFA concentration in the serum by lipolysis inhibition in the fatty tissue is also a sensible therapeutic principle for the treatment of diabetes mellitus. In accordance with investigations conducted by RANDLE and collaborators (RANDLE, P. J. in B. S. LEIBEL and G. A. WRENSHALL, Editors: On the Nature and Treatment of Diabetes, Excerpta Medica Foundation, Amsterdam-New York-London-Milan-Tokyo-Buenos Aires, p. 361, 1965), FFA's interfere with the utilization of glucose for the purpose of obtaining energy in the periphery of the body (musculature). Glucose absorption into the muscle cells is a process dependent on insulin. Since insulin simultaneously inhibits lipolysis and thus the transfer of FFA from the fatty tissue of the blood, the glucose utilization in the body periphery is disturbed for a dual reason in diabetes mellitus, which is characterized by restricted insulin secretion and production.

Primarily, the lack of insulin leads to a disturbance in the glucose absorption by the muscle cells. This disturbance is aggravated by the simultaneously increase in the FFA concentration in the blood and the concomitant, increased FFA fed to the body periphery. This factor is eliminated when lipolysis in the fatty tissue is pharmacologically inhibited; glucose utilization is improved and elevated blood glucose concentration is lowered. This has been shown in experiments on rats with insulin deficiency. FROESCH, WALDVOGEL, MEYER, JAKOB, and LABHART, Mol. Pharmacology, 3, 442, 1967. It can be confirmed in diabetics by improved glucose tolerance, a lowering of elevated blood glucose levels and a reduction of glucose in the urine. In this connection, agents inhibiting lipolysis either proved to be effective in monotherapy or were capable of again normalizing the derailed carbohydrate metabolism in secondary failures of therapy with β-cytotropic sulfonyl ureas and/or sulfonyl ureas and biguanides, in combination with these medicines. BERINGER, BAENDER, GLANINGER, MAYRHOFER, and SCHNACK, Horm. Metab. Res., 2, 81, 1970; GEYER and SOKOPP, Vienna, "Klin. Wschr." 81, 701, 1969; GEYER and SOKOPP, "Med. u. Ernaehr." 10, 115, 1969; NEUMANN, MICHAELIS, BIBERGEIL, and WULFERT, "Dtsch. Ges. Wesen" 27, 972, 1972.

Compounds heretofore used in such investigations as agents for inhibiting lipolysis, such as nicotinic acid, 3-pyridinemethanol, 5-(3-pyridyl)-tetrazole, 3,5-dimethylpyrazole, 3,5-dimethylisoxazole; the active metabolites 5-methylpyrazole-3-carboxylic acid and 5-methylisoxazole-3-carboxylic acid, formed in the organism from the two last-mentioned compounds; various other pyrazole and isoxazole derivatives; as well as a number of adenosine derivatives, effect an initial lowering of serum FFA. However, they cannot be employed for a long-term therapy of metabolic anomalies, for various reasons. Except for the adenosine derivatives, all above-mentioned compounds, especially nicotinic acid and compounds derived therefrom, after fading of their FFA-lowering activity, result in an increase of free fatty acids in the serum, overshooting the initial level (rebound phenomenon), thus nullifying the positive consequences of their initial effect. BIZZI and GARATTINI in: Metabolic Effects of Nicotinic Acid and Its Derivatives, Hans-Huber publishers, Berne, p. 207, 1971. Moreover, pyrazole and isoxazole derivatives, as well as pyridyltetrazole, lose their lipolysis-inhibiting capacity upon repeated application on successive days, after a shorter or longer period of time, and thus lose their ability to lower the concentration of FFA in the serum. This behavior, called tachyphylaxis, was observed in animal experiments. BIZZI and GARATTINI in: Metabolic Effects of Nicotinic Acid and Its Derivatives, Hans-Huber publishers, Berne, 1971, p. 207; FROESCH, WALDVOGEL, MEYER, JAKOB, and LABHART, Mol. Pharmacol. 3, 442, 1967; SCHILLINGER and LOGE, Biochem. Pharmacol., in print, 1974. It was confirmed in man during the clinical application of 5-methylpyrazole-3-carboxylic acid and 5-methylisozazole-3-carboxylic acid. NEUMANN, MICHAELIS, BIBERGEIL, and WULFERT, "Dtsch. Ges. Wesen" 27 972, 1972; GEYER and SOKOPP, Acta endocr. (Kbh.) Suppl. 173, 127, 1973. In accordance with the above-mentioned findings, the phenomenon of tachyphylaxis need not necessarily be related to the rebound phenomenon but, just as the latter, the former phenomenon is prohibitive for long term therapy.

Antilipolytically effective adenosine derivatives exhibit neither a rise in serum FFA, overshooting the starting level, after the initial reduction, nor a loss in effectiveness upon repeated administration. SCHILLINGER and LOGE, Biochem. Pharmacol., in print, 1974. However, these compounds possess only an extremely small therapeutic range, since they affect cardiac activity at lipolytically effective or only slightly higher doses, and lead to a drop in the heartbeat frequency. MANNESMANN, publication in preparation, 1974. Due to this dangerous effect on the cardiovascular system, adenosine derivatives cannot be used in long-term therapy in humans.

In the search for lipolysis-inhibiting agents suitable for a long-term administration to humans, it has been found, surprisingly, that the novel thiophene derivatives of this invention exhibit neither the phenomenon of tachyphylaxis nor that of overshooting the free fatty acid level after an initial reduction (rebound phenomenon). Moreover, no effect on heartbeat frequency was seen and the therapeutic dosage range is very great.

SUMMARY OF THE INVENTION

In a composition aspect, this invention relates to thiophene derivatives of general Formula

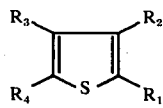

wherein one of $R_1$, $R_2$, $R_3$ and $R_4$ is $R_x$; 0, 1, or 2 thereof are $R_y$, and the remainder are hydrogen atoms, wherein $R_x$ is

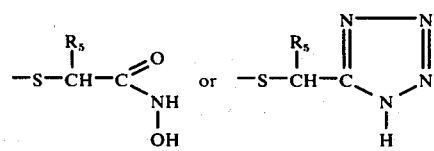

with $R_5$ being a hydrogen atom or alkyl of 1–6 carbon atoms, and $R_y$ is alkyl of 1–6 carbon atoms, alkoxy of 1–6 carbon atoms or a halogen atom, including, when $R_5$ is an alkyl group, their enantiomers; and their pharmacologically salt with inorganic and organic bases.

In another composition aspect, this invention relates to pharmaceutical compositions comprising a compound of this invention in admixture with a pharmaceutically acceptable carrier.

In process aspects, this invention relates to processes for the production and use as antilipolytic agents of the compounds of this invention.

DETAILED DISCUSSION

Specifically contemplated classes of compounds of this invention include those wherein:
a. $R_x$ is —S—$CHR_5$-5-tetrazolyl, especially those wherein $R_1$ is $R_x$;
b. $R_x$ is —S—$CHR_5$—CONHOH, especially those wherein $R_1$ is $R_x$;
c. those of (a) and (b) wherein $R_5$ is H or $CH_3$, preferably H;
d. those of (a), (b) and (c) wherein 3 of $R_1$, $R_2$, $R_3$ and $R_4$ are H;
e. those of (a), (b) and (c) wherein 2 of $R_1$, $R_2$, $R_3$ and $R_4$ are H;
f. those of (a), (b) and (c) wherein 1 of $R_1$, $R_2$, $R_3$ and $R_4$ are H;
g. those of (a), (b), (c), (e) and (f) wherein an $R_y$ is at the 5- position, especially those wherein the $R_y$ at the 5-position is $CH_3$, $C_2H_5$, $CH_3O$, Cl or Br;
h. those of (a), (b), (c), (e) and (f) wherein an $R_y$ is at the 4- position, especially those wherein $R_y$ at the 4- position is $CH_3$ or $CH_3O$;
i. each of (a) – (h) as a pharmaceutically acceptable salt with a base, preferably an organic base and especially methylglucamine.

The alkyl groups can be straight-chain or branched and saturated or unsaturated. Specific examples are methyl, ethyl, n-propyl, isopropyl, n-butyl, isobutyl-tert.-butyl, n-pentyl and n-hexyl, preferred being alkyl groups of 1–4 carbon atoms, which preferably are straight-chain.

The alkyl groups in the alkoxy groups correspond to the above alkyl groups. Specific examples are n-propoxy, isopropoxy, n-butoxy, isobutoxy, tert.-butoxy, n-pentoxy, n-hexyloxy and the preferred methoxy and ethoxy.

The halogen atoms include fluorine and iodine, but preferably are bromine and chlorine.

The pharmacologically acceptable salts of this invention include salts of both inorganic and organic bases and are those customarily employed by those skilled in the art for the salt formation. Examples of suitable bases are sodium hydroxide, potassium hydroxide, calcium hydroxide, magnesium hydroxide, glucamine, N-methylglucamine, N,N-dimethylglucamine, ethanolamine, diethanolamine, 2-amino-2-hydroxymethyl-1,3-propanediol and morpholine.

In a process aspect, this invention relates to processes for the production of thiophene derivatives of general Formula I and their salts with bases wherein:

a compound of general Formula II

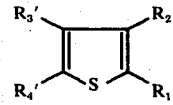

wherein one of $R_1'$, $R_2'$, $R_3'$ and $R_4'$ is a —S—H-group; 0, 1 or 2 thereof are $R_y$, and the remainder are hydrogen atoms, or an alkali metal salt of the thiol, a. is reacted, to produce compounds of general Formula I wherein $R_x$ is —S—$CHR_5$—CONHOH, with a halogen ester of general Formula III

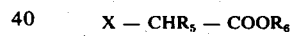

wherein $R_5$ has the above given values, X is a halogen atom, and $R_6$ is alkyl of 1–4 carbon atoms, and the thus-obtained ester is reacted with hydroxylamine or a salt thereof to produce the corresponding hydroxamic acid derivative; or b. is reacted, to produce compounds of general Formula I wherein $R_x$ is —S—$CHR_5$-5-tetrazolyl, with a halogen nitrile of the general Formula IV

wherein X and $R_5$ have the above values given, and the thus-obtained nitrile is reacted with alkali azide to produce the corresponding tetrazole derivative; and, optionally thereafter, the compound of Formula I obtained according to (a) or (b) is subjected to a racemate splitting step and/or is converted with a base into the respective, pharmacologically acceptable salt.

Alkali salts of the thiols of general Formula III include sodium and potassium salts, but preferably are lithium salts.

Preferred halogen atoms in the halogen esters and halogen nitriles are chlorine and bromine.

The reaction of the thiol or of an alkali salt thereof with the halogen ester according to procedure (a) is conducted in the presence of an inert organic solvent, preferably an ether, such as, for example, diethyl ether or tetrahydrofuran. The halogen ester is added at a temperature of from −50° to 0° C, preferably about −20° C. After the ester has been added, the reaction mixture is agitated for several hours at temperatures of from room temperature to the boiling point of the solvent employed.

The reaction of the ester with hydroxylamine, which is preferably employed as hydroxylamine hydrochloride, according to procedure (a) is conducted either in an aqueous alkaline solution or under anhydrous conditions in alcohol, preferably methanol or ethanol, with the addition of alkali alcoholate, preferably sodium methylate, sodium ethylate, potassium methylate or potassium ethylate, at temperatures of from 0° to 40° C, preferably about room temperature.

The reaction of the thiol or of an alkali salt thereof with a halonitrile according to procedure (b) is conducted essentially like the reaction with the halogen ester, except the temperature should not exceed 40° C during the course of the reaction. The reaction of the nitrile with an alkali azide is carried out either in a solvent, e.g., toluene, at temperatures of above 100° C, or in ethanol, propanol or butanol at boiling temperature, but preferably in dimethylformamide at temperatures of above 100° C, preferably 120° to 140° C, with the addition of lithium chloride and/or ammonium chloride, or preferably in solvents, such as, for example, dimethylformamide or hexamethylphosphoric triamide, in the presence of a weak organic carboxylic acid, e.g., acetic acid or formic acid.

If products are obtained during the course of the process which contain an asymmetrical carbon atom, the primarily obtained racemic products can optionally be separated in accordance with known methods into the optically active forms thereof. Since the products of the process are sufficiently acidic, the racemic primary product is suitably converted into the salt thereof with an optically active base, and the respective optically active enantiomers are separated by fractional crystallization. After separation is effected, the optically active compound of Formula I is liberated from its salt in the usual manner. Preferred optically active bases include brucine, strychnine, α-phenylethylamine, and similar compounds.

The thiols and the alkali salts thereof employed as the starting materials are either known from the literature or can be prepared according to methods known in the literature.

It is especially advantageous to lithiate a correspondingly substituted thiophene derivative with butyllithium and then convert the product with sulfur into the thiol. This process has the advantage that the thiol, obtained as its lithium salt, need not be isolated, but rather can be further processed immediately.

The novel compounds of this invention are suitable for lowering of the free fatty acid levels in the blood plasma of animals and humans, including long range therapy, without incurring, after an initial reduction, a rise which exceeds the original values, and without undesired and/or damaging effects on the cardiovascular system. The compounds thus can be used for the treatment of metabolic diseases such as, for example, diabetes mellitus, hyperlipemia, and arterioscleroisis. In the treatment of diabetes mellitus, this treatment possibility can be added as a fourth possibility of equivalent value to the three customary drug therapies, viz., insulin, sulfonylamino compounds and biguanides.

The compounds of this invention have special significance in combination therapy with the medicinal agents conventionally utilized in the treatment of diabetes mellitus.

The tables set forth below contain a comparison of the FFA reduction after one-time administration ("one day profile") and in the profile of FFA reduction after daily administration for several days ("tachyphylaxis profile") of several compounds of this invention and known compounds as the standard, viz., 5-methylisoxazole-3-carboxylic acid or 5-methylpyrazole-3-carboxylic acid.

The compounds of this invention significantly reduce, after one-time oral administration, the free fatty acids (FFA) in the serum of fasting rats, as can be seen from Tables A, B and C, using as examples of compounds of this invention, (2-thienylthio)-acetohydroxamic acid and (2-thienyl)-(5-tetrazolylmethyl)-sulfide and as comparison compound the conventional 5-methylpyrazole-3-carboxylic acid. In the compounds of this invention, an initial lowering of the FFA content is not followed by the undesirable resumption of the increase in FFA observed after treatment with 5-methylpyrazole-3-carboxylic acid. This "rebound" phenonomen, also observed in other conventional lipolysis-inhibiting agents, is independent of dosage and nullifies the positive results of the initial reduction and renders the therapeutic value of such a compound doubtful.

Table D illustrates the antilipolytic effect of (2-thienylthio)-acetohydroxamic acid after treatment for several days. The compounds shows, after a period of five days, i.e., at a point in time where the reference compound 5-methylisoxazole-3-carboxylic acid no longer reduces FFA, unchanged antilipolytic activity. This lack of tachyphylactic effects, which is characteristic of compounds of this invention, is a absolute prerequisite for long-term administration of a lipolysis-inhibiting agent.

TABLE A

One-day profile of the free fatty acids (FFA) in the serum of rats fasting for 24 hours after oral treatment with (2-thienylthio)-acetohydroxamic acid (I) and 5-methylpyrazole-3-carboxylic acid (II) as compared to the untreated control group (III).

| Average Values of 10 Animals: | | |
| FFA After (Hours) | FFA in meq./l. After I, 50 mg/kg | II, 5 mg/kg | III |
|---|---|---|---|
| 0.5 | 0.845 | 0.350 | 1.150 |
| 1 | 0.715 | 0.330 | 1.055 |
| 2 | 0.620 | 0.355 | 0.945 |
| 3 | 0.855 | 0.395 | 1.115 |
| 4 | 1.055 | 0.730 | 1.640 |
| 5 | 0.730 | 0.605 | 0.875 |
| 6 | 1.130 | 1.560 | 1.450 |
| 7 | 0.605 | 1.025 | 0.775 |
| 9 | 0.610 | 1.150 | 0.940 |
| 11 | 0.785 | 1.315 | 1.045 |
| 13 | 0.640 | 1.170 | 1.140 |
| 16 | 0.990 | 1.315 | 1.370 |
| 19 | 0.835 | 0.985 | 0.850 |
| 24 | 0.745 | 0.825 | 0.910 |

___ : Significantly different from the control group.

TABLE B

One-day profile of the free fatty acids (FFA) in the serum of rats fasting for 24 hours after oral treatment with (2-thienlthio)-acetohydroxamic acid (I) and 5- methylpyrazole-3-carboxylic acid (II) as compared to the untreated control group (III).

TABLE C

One-day profile of the free fatty acids (FFA) in the serum of rats fasting for 24 hours after oral treatment with (2-thienyl)-(5-tetrazolymethyl)-sulfide (I) and 5-methylpyrazole-3-carboxylic acid (II) as compared to the untreated control group (III).

| Average Values of 10 Animals: | | | |
|---|---|---|---|
| FFA After (Hours) | I, 10 mg/kg | FFA in meq./l. After II, 5 mg/kg | III |
| 1 | 0.775 | 0.215 | 0.945 |
| 3 | 0.705 | 0.350 | 0.870 |
| 5 | 0.955 | 0.940 | 1.335 |
| 7 | 0.915 | 1.320 | 0.910 |
| 9 | 0.645 | 1.460 | 0.980 |
| 16 | 1.195 | 1.270 | 1.300 |
| 19 | 1.100 | 1.205 | 1.160 |
| 24 | 0.875 | 1.070 | 1.095 |

____ : Significantly different from the control group.

| Average Values of 9 Animals: | | | |
|---|---|---|---|
| FFA After (Hours) | I, 50 mg/kg | FFA in meq./l. After II, 5 mg/kg | III |
| 0 | 1.168 | 1.188 | 1.296 |
| 1 | 0.547 | 0.304 | 1.054 |
| 2 | 0.551 | 0.260 | 0.977 |
| 4 | 0.598 | 0.497 | 1.004 |
| 7 | 0.632 | 1.167 | 0.994 |
| 9 | 0.660 | 1.344 | 1.019 |
| 14 | 1.082 | 1.206 | 1.001 |
| 19 | 0.853 | 0.951 | 0.943 |
| 24 | 0.692 | 0.805 | 0.862 |

____ : Significantly different from the control group.

TABLE D

FFA-lowering effect of (2-thienylthio)-acetohydroxamic acid (I) and 5-methylisoxazole-3-carboxylic acid (II) as compared to the untreated control group (III) on the first and fifth days of oral treatment of rats fasting for 24 hours (tachyphylaxis test).

| | | FFA in Meq./l. Serum | |
|---|---|---|---|
| | | Day 1 | Day 5 |
| I | (50 mg./kg.) | 0.66 | 0.49 |
| II | (1 mg./kg.) | 0.41 | 0.73 |
| III | | 0.84 | 0.81 |

____ : Significantly different from the control group.

The compounds of this invention can be administered orally or parenterally. The processing into forms of application can be accomplished without additives or together with the pharmaceutically acceptable additives, vehicles, flavor-ameliorating agents, and others customary in galenic pharmacy, for example, in powder form, as tablets, dragees, capsules, pills, or in the form of suspensions or solutions.

The amount of active agent administered generally is about 1 to about 100 mg./kg., preferably 1 to 30 mg./kg. body weight, per day. Dosage units usually contain about 10 mg. to 1 g., preferably 50–550 mg., of active agent.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

(2-Thienyl)-(5-tetrazolylmethyl)-sulfide

A mixture of 7.76 g. (50 millimoles) of thiophene-2-thioacetonitrile, 4.30 g. (66 millimoles) of sodium azide, 3.55 g. (66 millimoles) of ammonium chloride, and 0.38 g. (9 millimoles) of lithium chloride is maintained for 5 hours at 120° in 50 ml. of dry dimethylformamide. The dimethylformamide is withdrawn under vacuum, the residue is combined with 500 ml. of cold 0.2 N sodium hydroxide solution and extracted with ether. The aqueous phase is adjusted to pH 3 and extracted three times with respectively 150 ml. of ether. The ether phase yields, after drying ($Na_2SO_4$) and concentration, the crude, solid tetrazole which is recrystallized once from acetonitrile/water and once from ethanol/water.

Melting point: 130°; yield: 14% of theory.

Preparation of thiophene-2-thioacetonitrile

Under agitation, 100 ml. of approximately 22% strength (about 230 mmol) of butyllithium solution (in hexane) is added quickly dropwise to 22.7 g. (270 mmol) of thiphene in 50 ml. of dry ether at −40°. The apparatus is purged with dry nitrogen during this step. After 2 hours at room temperature, the mixture is cooled to −70° and, during the course of 15 minutes, 7.5 g. (234 mmol) of sulfur is added via a solids metering funnel. After this step, the mixture is allowed to come to a temperature of 0 °, maintained for 30 minutes at this temperature, cooled to −10° to −20°, and then 17.4 g. (230 mmol) of chloroacetonitrile in 50 ml. of ether is added dropwise thereto. The mixture is agitated for 1½ hours at room temperature and for 15 minutes under reflux and then poured into 500 ml. of 1 N cold hydrochloric acid. The organic phase is separated, the aqueous phase is extracted with ether, and the combined organic phases are extracted with 100 ml. of concentrated sodium bicarbonate solution and then three times with respectively 200 ml. of water. After drying over sodium sulfate, the ether and hexane are removed under vacuum and the residue is fractionated.

B.p.$_{0.5}$: 85°–88°; yield: 46% of theory (based on chloracetonitrile).

EXAMPLE 2

(5-Methyl-2-thienyl)-(5-tetrazolylmethyl)-sulfide

The compound is produced analogously to Example 1 from 5-methyl-2-thienylthioacetonitrile (b.p.$_{0.001}$: 78°–82°) and sodium azide.

M.p.: 146° (propanol); yield: 22% of theory.

5-Methyl-2-thienylthioacetonitrile is produced analogously to Example 1 from 2-methylthiophene, butyllithium, sulfur, and chloracetonitrile. The metalizing step is in this case conducted in tetrahydrofuran.

B.p.$_{0.001}$: 78°–82°; yield: 58% of theory.

EXAMPLE 3

(5-Methoxy-2-thienyl)-(5-tetrazolylmethyl)-sulfide

This compound is prepared analogously to Example 1 from 5-methoxy-2-thienylthioacetonitrile (b.p.$_{0.05}$: 105°–109°) and sodium azide.

M.p.: 132°–133° (propanol); yield: 36% of theory.

5-Methoxy-2-thienylthioacetonitrile is produced analogously to Example 1 from 2-methoxythiophene, butyllithium, sulfur, and chloroacetonitrile.

B.p.$_{0.05}$: 105°–109°; yield: 27% of theory.

EXAMPLE 4

(5-Methoxy-2-thienyl)-[1-(5-tetrazolyl)-ethyl]-sulfide

This compound is produced analogously to Example 1 from 2-(5-methoxy-2-thienylthio)-propionitrile (b.p.$_{0.001}$: 92°–94°) and sodium azide.

M.p.: 116°–117° (n-propanol/hexane); yield: 23% of theory.

2-(5-Methoxy-2-thienylthio)-propionitrile is prepared in analogy to Example 1 from 2-methoxythiophene, butyllithium, sulfur, and α-bromopropionitrile.

B.p.$_{0.001}$: 92°–94°; yield: 68% of theory.

EXAMPLE 5

(5-Bromo-4-methyl-2-thienyl)-(5-tetrazolylmethyl)-sulfide 15.7 g. (63 mmol) of [(5-bromo-4-methyl)-2-thienylthio]-acetonitrile, 16.35 g. (252 mmol) of sodium azide, and 23.2 g. (504 mmol) of formic acid are agitated in 200 ml. of anhydrous hexamethylphosphoric triamide for 40 hours at 60°.

The mixture is poured on 200 g. of ice and combined with 1,000 ml. of 0.5 N NaOH. The hexamethylphosphoric triamide is extracted with chloroform (three times respectively 250 ml.), acidified to pH 3, and the tetrazole is extracted with ether (three times respectively 500 ml.). The ether phases are dried over Na$_2$SO$_4$, treated with active carbon, and concentrated. The remaining solid residue is recrystallized once from benzene.

M.p.: 148° (benzene); yield: 93% of theory. [(5-Bromo-4-methyl)-2-thienylthio]-acetonitrile is prepared analogously to Example 1 from 2,5-dibromo-3-methylthiophene, butyllithium, sulfur, and chloracetonitrile.

B.p.$_{0.06}$: 117°; yield: 68% of theory.

2.5-Dibromo-3-methylthiophene is obtained by brominating 3-methylthiophene in glacial acetic acid at 0°.

B.p.$_{12}$: 102°; yield: 82% of theory.

EXAMPLE 6

Methylglucamine Salt of (5-Bromo-4-methyl-2-thienyl)-(5-tetrazolymethyl)-sulfide The salt is crystallized from a mixture of 291 mg. (1 mmol) of the sulfide and 195 mg. (1mmol) of N-methylglucamine in 5 ml. of carbon tetrachloride after the addition of ether.

M.p.: 131°; yield: 81% of theory.

Example 7

(3,4-Dimethyl-2-thienyl)-(5-tetrazolylmethyl)-sulfide

The compound is produced analogously to Example 5 from [(3,4-dimethyl)-2-thienylthio]-acetonitrile, sodium azide, formic acid, and hexamethylphosphoric triamide. The compound is obtained as a brown oil which could not be made to crystallize. The mass spectrum carresponds to the indicated structure. Yield: 7% of theory.

[(3,4-Dimethyl)-2-thineylthio]-acetonitrile is produced in correspondence with Example 1 from 3,4-dimethylthiophene (b.p.$_{0.05}$: 150°; bulb tube distillation), butyllithium, sulfur, and bromoacetonitrile. The oily crude product, pure as determined by thin-layer chromatography, is utilized without distillation in the ring closure reaction with sodium azide.

EXAMPLE 8

(3-Thienyl)-(5-tetrazolylmethyl)-sulfide

This compound is prepared analogously to Example 5 from (3-thienylthio)-acetonitrile, sodium azide, and formic acid in hexamethylphosphoric triamide.

M.p.: 102°–104° (acetonitrile); yield: 8% of theory.

(3-Thienylthio)-acetonitrile is prepared analogously to Example 1 from 3-bromothiophene, butyllithium, sulfur, and chloroacetonitrile. B.p.$_{0.04}$: 105°–115°; yield: 58% of theory.

EXAMPLE 9

(5-Chloro-2-thienyl)-(5-tetrazolylmethyl)-sulfide

The compound is obtained analogously to Example 1 from (5-chloro-2-thienylthio)-acetonitrile and sodium azide.

M.p.: 135°–136° (from ethyl acetate/petroleum ether); yield: 51% of theory.

(5-Chloro-2-thienyl)-acetonitrile is obtained in analogy to Example 1 from 2,5-dichlorothiophene, butyllithium, sulfur, and bromoacetonitrile.

B.p.$_{0.1}$: 95°–99°; yield: 30% of theory.

EXAMPLE 10

(3,4-Dimethoxy-2-thienyl)-(5-tetrazolylmethyl)-sulfide

The compound is prepared in accordance with Example 5 from (3,4-dimethoxy-2-thienylthio)-acetonitrile, formic acid, and sodium azide in hexamethylphosphoric triamide.

M.p.: 129° (water); yield: 67% of theory.

(3,4-Dimethoxy-2-thienylthio)-acetonitrile is produced analogously to Example 1 from 3,4-dimethoxythiophene, butyllithium, sulfur, and chloroacetonitrile. The compound is used without distillation as a crude product in the ring closure reaction.

EXAMPLE 11

(2-Thienylthio)-acetohydroxamic Acid

A mixture of 13.8 g. (60 mmol) if thiophene-2-thioacetic acid butyl ester, 5.25 g. (75 mmol) of hydroxylamine hydrochloride, 6.0 g. (150 mmol) of NaOH, and 120 ml. of H$_2$O is vigorously agitated for 20 hours. The aqueous-alkaline phase is extracted with ether to remove unreacted ester and is then combined with solid ammonium chloride to pH 8. After 2 hours, the mixture is vacuum-filtered, the crude hydroxamic acid is reprecipitated once with acetic acid from 10% soda solution and recrystallized from acetone/carbon tetrachloride.

M.p.: 108°–109° (acetone/carbon tetrachloride); yield: 17% of theory.

Butyl Ester of Thiophene-2-thioacetic Acid

Starting with 22.7 g. (270 mmol) of thiophene, the process is conducted, up to the sulfur addition, as described in the preparation of thiophene-2-thioacetonitrile (Example 1). After adding the sulfur, the mixture is maintained at 0° for 30 minutes, then cooled to −20°, and at this temperature 40.6 g. (270 mmol) of butyl chloroacetate is added dropwise thereto. The mixture is held at room temperature for 1 ½ hours and then refluxed for 1 hour. The mixture is poured into 500 ml. of ice-cold hydrochloric acid, extracted three times with respectively 200 ml. of ether, the ether phases are washed with water, dried over sodium sulfate, the ether is distilled off, and the remaining oil is distilled under vacuum.

B.p.$_{0.5}$: 115°–116°; yield: 81% of theory.

EXAMPLE 12

(4-Methyl-2-thienylthio)-acetohydroxamic Acid

This compound is prepared analogously to Example 11 from (4-methyl-2-thienylthio)-acetic acid methyl ester, hydroxylamine hydrochloride, and sodium hydroxide solution.

M.p.: 99.5° (ethyl acetate); yield: 21% of theory.

The methyl ester of (4-methyl-2-thienylthio)-acetic acid is prepared analogously to Example 11 from 3-methylthiophene, butyllithium, sulfur, and methyl chloroacetate.

B.p.$_{0.01}$: 92°–99°; yield: 65% of theory.

EXAMPLE 13

2-(2-Thienylthio)-propiohydroxamic Acid

This compound is produced in analogy to Example 11 from ethyl 2-(2-thienylthio)-propionate, hydroxylamine hydrochloride, and sodium hydroxide solution.

M.p.: 121°–122° (ethyl acetate); yield: 21% of theory.

Ethyl 2-(2-thienylthio)-propionate is produced analogously to Example 11 from thiophene, butyllithium, sulfur, and the ethyl ester of α-bromopropionic acid.

B.p.$_{0.03}$: 86°; yield: 64% of theory.

EXAMPLE 14

(5-Ethyl-2-thienylthio)-acetohydroxamic Acid

This compound is prepared in accordance with Example 11 from the methyl ester of (5-ethyl-2-thienylthio)-acetic acid, hydroxylamine hydrochloride, and sodium hydroxide solution, adding to the charge (40 mmol of ester) 40 ml. of dioxane as the solubilizer. For purposes of working up the reaction mixture, the latter is first concentrated to dryness, then taken up in 80 ml. of water, extracted with ether, and then combined with solid ammonium chloride, whereupon the mixture is worked up as described in Example 11. The (5-ethyl-2-thienylthio)-acetic acid still present in the crude product is removed by digestion with concentrated NaHCO$_3$ solution, and the solid, dried residue is recrystallized from acetonitrile.

M.p.: 89°–90° (acetonitrile); yield: 11% of theory.

The methyl ester of (5-ethyl-2-thienylthio)-acetic acid is prepared analogously to Example 11 from 2-ethylthiophene, butyllithium, sulfur, and methyl chloroacetate.

B.p.$_{0.4}$: 107°–109°; yield: 79% of theory.

EXAMPLE 15

2-(2-Thienylthio)-valerohydroxamic Acid

A mixture of 19.5 g. (80 mmol) of the ethyl ester of 2-(2-thienylthio)-valeric acid, 7.0 g. (100 mmol) of hydroxylamine hydrochloride, 8.0 g. (200 mmol) of NaOH, 160 ml. of water, and 100 ml. of ethanol is agitated for 30 hours at room temperature. The mixture is then concentrated to 80 ml., extracted twice with 100 ml. of ether, and the aqueous-alkaline phase is combined with solid ammonium chloride to pH 8. The thus-separated oil is solidified in an ice bath. After digestion with concentrated NaHCO$_3$ solution, the solid residue is vacuum-filtered, washed with water, and recrystallized from acetonitrile.

M.p.: 134°–135° (acetonitrile); yield: 27% of theory.

The ethyl ester of 2-(2-thienylthio)-valeric acid is produced analogously to Example 11 from thiophene, butyllithium, sulfur, and ethyl α-bromovalerate.

B.p.$_{0.03}$: 105°–107°; yield: 75% of theory.

EXAMPLE 16

2-(3,5-Dibromo-2-thienylthio)-acetohydroxamic Acid

This compound is prepared analogously to Example 11 from the methyl ester of 2-(3,5-dibromo-2-thienylthio)-acetic acid, hydroxylamine hydrochloride, and sodium hydroxide solution.

M.p.: 121°–122° (acetonitrile/water); yield: 9% of theory.

The methyl ester of 2-(3,5-dibromo-2-thienylthio)-acetic acid is prepared as described in Example 11 from 2,3,5-tribromothiophene, butyllithium, sulfur, and methyl chloroacetate. After pouring the reaction mixture into dilute hydrochloric acid, the mixture is extracted three times with ether and the organic phase extracted three times with respectively 50 ml. of saturated NaHCO$_3$ solution and three times with respectively 50 ml. of saturated NaCl solution. After drying over Na$_2$SO$_4$, the ether is removed under vacuum and the ester, which is uniform according to thin-layer chromatography, is used directly without distillation in the reaction to form hydroxamic acid.

EXAMPLE 17

(3-Methoxy-2-thienylthio)-acetohydroxamic Acid

This compound is produced analogously to Example 11 from the methyl ester of (3-methoxy-2-thienylthio)-acetic acid, hydroxylamine hydrochloride, and sodium hydroxide solution.

M.p.: 134°–135° (ethyl acetate); yield: 19% of theory.

The methyl ester of (3-methoxy-2-thienylthio)-acetic acid is prepared analogously to Example 11 from 3-methoxythiophene, butyllithium, sulfur, and chloroacetic acid.

B.p.$_{0.03}$: 120°–130°; yield: 64% of theory.

EXAMPLE 18

(3-Thienylthio)-acetohydroxamic Acid

This compound is produced as described in Example 11 from the methyl ester of (3-thienylthio)-acetic acid, hydroxylamine hydrochloride, and sodium hydroxide solution.

M.p.: 108°–109° (ethyl acetate); yield: 18% of theory.

The methyl ester of (3-thienylthio)-acetic acid is produced in accordance with Example 11 from 3-bromothiophene, butyllithium, sulfur, and methyl bromoacetate.

B.p.$_{0.03}$: 102°–104°; yield: 65% of theory.

EXAMPLE 19

(5-Methoxy-2-thienylthio)-acetohydroxamic Acid 2.62 g. (12 mmol) of the methyl ester of (5-methoxy-2-thienylthio)-acetic acid and 1.26 g. (18 mmol) of hydroxylamine hydrochloride in 15 ml. of ethanol are added to a sodium ethylate solution of 0.41 g. (18 mmol) of sodium in 15 ml. of ethanol. The mixture is stirred for 24 hours at room temperature and then concentrated to dryness. The mixture is then taken up in 200 ml. of 5% soda solution, extracted three times with respectively 150 ml. of ether, and the aqueous-alkaline phase is combined first with 1 N HCl and then with solid ammonium chloride to pH 8.5. The thus-precipitated hydroxamic acid is freed of traces of concomitantly precipitated (5-methoxy-2-thienylthio)-acetic acid by digestion with concentrated sodium bicarbonate solution and recrystallized from ethyl acetate/petroleum ether.

M.p.: 90°–91° (ethyl acetate/petroleum ether); yield: 11% of theory.

The methyl ester of (5-methoxy-2-thienylthio)-acetic acid is produced analogously to Example 11 from 2-methoxy-thiophene, butyllithium, sulfur, and methyl chloroacetate.

B.p.$_{0.03}$: 114°–119°; yield: 41% of theory.

EXAMPLE 20

Methylglucamine Salt of (2-Thienylthio)-acetohydroxamic Acid

The salt is crystallized from a mixture of 250 mg. (1.32 mmol) of the hydroxamic acid and 251 mg. (1.32 mmol) of N-methylglucamine in 5 ml. of ethanol. M.p.: 127°–128° (ethanol); yield: 47% of theory.

EXAMPLE 21

500 g. of (2-thienylthio)-acetohydroxamic acid, 3 g. of disperse silicic acid ("Aerosil"), and 47 g. of corn starch are screened, mixed homogeneously, and filled into hard gelatin capsules with a net filling of 550 mg./capsule.

EXAMPLE 22

500 g. of (2-thienyl)-(5-tetrazolylmethyl)-sulfide, 3 g. of disperse silicic acid (Aerosil), 45 g. of corn starch, 50 g. of dry binder cellulose ("Avicel PH 101"), and 2 g. of magnesium stearate are mixed homogeneously and pressed into tablets of 600 mg. in the usual way on a tabletting press. The tablets are then provided with a coating lacquer consisting of 8 parts of hydroxypropylcellulose ("Klucel LF"), one part of castor oil, and one part of talc.

The preceding exammples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usage and conditions.

What is claimed is:

1. A thiophene derivative of the formula

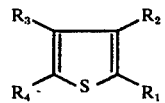

wherein one of $R_1$, $R_2$, $R_3$ and $R_4$ is $R_x$; 0, 1, or 2 thereof are $R_y$, and the remainder thereof are hydrogen atoms, wherein $R_x$ is —S—CHR$_5$—CONHOH wherein $R_5$ is a hydrogen atom or alkyl of 1—6 carbon atoms, and wherein $R_y$ is alkyl of 1–6 carbon atoms, alkoxy of 1–6 carbon atoms or a halogen atom, including, when $R_5$ is an alkyl group, their enantiomers, and pharmacologically acceptable salts thereof with inorganic and organic bases.

2. A compound of claim 1, wherein $R_1$ is —S—CHR$_5$—L—CONHOH.

3. A compound of claim 2, wherein $R_5$ is H.

4. A compound of claim 1, wherein 3 of $R_1$, $R_2$, $R_3$ and $R_4$ are H.

5. A compound of claim 1, wherein 2 of $R_1$, $R_2$, $R_3$ and $R_4$ are H.

6. A compound of claim 1, wherein 1 of $R_1$, $R_2$, $R_3$ and $R_4$ is H.

7. A compound of claim 1, (2-thienylthio)-acetohydroxamic acid.

8. A compound of claim 1, (4-methyl-2-thienylthio)-acetohydroxamic acid.

9. A compound of claim 1, 2-(2-thienylthio)-propiohydroxamic acid.

10. A compound of claim 1, (5-ethyl-2-thienylthio)-acetohydroxamic acid.

11. A compound of claim 1, 2-(2-thienylthio)-valerohydroxamic acid.

12. A compound of claim 1, 2-(3,5-dibromo-2-thienylthio)-acetohydroxamic acid.

13. A compound of claim 1, (3-methoxy-2-thienylthio)-acetohydroxamic acid.

14. A compound of claim 1, (3-thienylthio)-acetohydroxamic acid.

15. A compound of claim 1, (5-methoxy-2-thienylthio)-acetohydroxamic acid.

16. A compound of claim 1, methylglucamine salt of (2-thienylthio)-acetohydroxamic acid.

17. A pharmaceutical composition comprising an amount per unit dosage of a compound of claim 1 effective to lower abnormally high serum free fatty acid levels, in admixture with a pharmaceutically acceptable carrier.

18. A method of inhibiting lipolysis which comprises administering systemically to a patient with an abnormally high serum free fatty acid level an amount of a compound of claim 1 effective to lower the free fatty acid level.

* * * * *